United States Patent
Clark et al.

(10) Patent No.: US 9,302,952 B2
(45) Date of Patent: Apr. 5, 2016

(54) ALKYLATION UNIT AND PROCESS RELATING THERETO

(75) Inventors: Mark A. Clark, West Columbia, TX (US); Jason J. Gislason, Katy, TX (US)

(73) Assignee: UOP LLC, Des Plaines, IL (US)

(*) Notice: Subject to any disclaimer, the term of this patent is extended or adjusted under 35 U.S.C. 154(b) by 933 days.

(21) Appl. No.: 13/550,197

(22) Filed: Jul. 16, 2012

(65) Prior Publication Data
US 2012/0279848 A1 Nov. 8, 2012

Related U.S. Application Data

(62) Division of application No. 12/236,761, filed on Sep. 24, 2008, now Pat. No. 8,246,921.

(51) Int. Cl.
*C07C 1/00* (2006.01)
*C07C 2/62* (2006.01)

(52) U.S. Cl.
CPC .......... *C07C 2/62* (2013.01); *C07C 2527/1206* (2013.01)

(58) Field of Classification Search
CPC ........................................................ B01J 10/00
USPC ................ 585/240, 700, 711, 733; 422/211; 208/67
See application file for complete search history.

(56) References Cited

U.S. PATENT DOCUMENTS

| | | | | |
|---|---|---|---|---|
| 3,864,423 A | * | 2/1975 | Chapman | 585/703 |
| 3,911,043 A | * | 10/1975 | Anderson | 585/716 |
| 3,919,342 A | * | 11/1975 | Chapman | 585/703 |
| 4,073,823 A | * | 2/1978 | Vora | 585/719 |
| 4,316,998 A | * | 2/1982 | Van Pool | 585/712 |
| 4,579,998 A | * | 4/1986 | Hutson, Jr. | 585/716 |
| 5,098,668 A | * | 3/1992 | Callen et al. | 422/111 |
| 5,284,990 A | * | 2/1994 | Peterson et al. | 585/709 |
| 2010/0076096 A1 | * | 3/2010 | Calis et al. | 518/702 |

* cited by examiner

*Primary Examiner* — Nina Bhat
(74) *Attorney, Agent, or Firm* — James C. Paschall

(57) ABSTRACT

One exemplary embodiment can be an alkylation unit. The alkylation unit can include at least one alkylation reaction zone having an alkylation catalyst, at least one cooler communicating with the at least one alkylation reaction zone, a settler communicating with the at least one alkylation reaction zone and the at least one cooler, a fractionation zone receiving an effluent from the settler passing through a line, and a boot coupled to a substantially horizontal portion of the line. Generally, the boot receives an effluent portion rich in the alkylation catalyst.

6 Claims, 4 Drawing Sheets

ALKYLATION UNIT AND PROCESS RELATING THERETO

CROSS-REFERENCE TO RELATED APPLICATION

This application is a Division of copending application Ser. No. 12/236,761 filed Sep. 24, 2008 now, U.S. Pat. No. 8,246,921, the contents of which are hereby incorporated by reference in its entirety.

FIELD OF THE INVENTION

This invention generally relates to an alkylation unit and process relating thereto.

DESCRIPTION OF THE RELATED ART

Typically, motor fuels are produced with sufficient octane to ensure the efficient and reliable operation of a motor vehicle. One process that can be used to improve motor fuel octane is an alkylation process. Generally, an alkylation process can combine light olefins, which are usually mixtures of propylene and butylenes, with one or more paraffins, such as isobutane. The alkylation reaction generally takes place in the presence of a catalyst, which may include an acid, under conditions typically selected to maximize alkylate yield and quality. Usually, the product can possess anti-knock properties and high octane due to the presence of branched alkanes.

In such processes, the reaction product may form a suspension with an alkylation catalyst and be transferred to downstream equipment for separating the alkylation catalyst from the reaction product. Usually, the reaction product is subsequently separated into various fractions typically using one or more distillation towers.

Unfortunately, the alkylation catalyst can carry over to the downstream distillation towers due to excessive throughput and/or undersized upstream separation vessels. In the instance that the alkylation catalyst may include, e.g., an acid, the transfer of the alkylation catalyst downstream can result in the corrosion and subsequent deterioration of the downstream equipment, such as the distillation towers. Such damage can increase maintenance costs and shorten equipment service life. As a consequence, it is desirable to minimize alkylation catalyst carry over to downstream vessels to minimize corrosion and wear.

Thus, it would be highly desirable to provide a unit or process that prevents the corrosion and wear of the downstream vessels due to alkylation catalyst carry over.

SUMMARY OF THE INVENTION

One exemplary embodiment can be an alkylation unit. The alkylation unit can include at least one alkylation reaction zone having an alkylation catalyst, at least one cooler communicating with the at least one alkylation reaction zone, a settler communicating with the at least one alkylation reaction zone and the at least one cooler, a fractionation zone receiving an effluent from the settler passing through a line, and a boot coupled to a substantially horizontal portion of the line. Generally, the boot receives an effluent portion rich in the alkylation catalyst.

Another exemplary embodiment can be a process. The process may include providing one or more hydrocarbons and an alkylation catalyst through a line. Typically, the line is coupled to a pipe to remove at least a portion of a settled alkylation catalyst, and the line is orientated substantially horizontal proximate to the pipe.

Yet another exemplary embodiment can be an alkylation unit. The alkylation unit can include one or more vessels receiving one or more hydrocarbons and an alkylation catalyst, and a fractionation zone communicating with the one or more vessels. Usually, an effluent from the one or more vessels communicates with a pipe for receiving a settled alkylation catalyst coupled to a line having a substantially horizontal portion proximate to the pipe before entering the fractionation zone.

As described herein, the disclosed embodiments can provide at least one mechanism or device for separating the alkylation catalyst from the one or more hydrocarbons upstream of a fractionation zone. As such, the at least one mechanism or device can remove the alkylation catalyst and minimize corrosion and subsequent deterioration of the downstream equipment. In some instances, the embodiments disclosed herein can economically modify an existing alkylation unit to remove alkylation catalyst that would otherwise carry over to downstream equipment.

DEFINITIONS

As used herein, hydrocarbon molecules may be abbreviated $C_1, C_2, C_3 \ldots C_n$ where "n" represents the number of carbon atoms in the one or more hydrocarbon molecules.

As used herein, the term "rich" can mean an amount of generally at least about 50%, and preferably about 70%, by mole, of a compound or class of compounds in a stream.

As used herein, the term "substantially" can mean an amount of generally at least about 80%, preferably about 90%, and optimally about 99%, by mole, of a compound or class of compounds in a stream.

As used herein, the term "effluent" may be used to refer to a stream exiting one of several vessels upstream of a fractionation zone. Typically, the effluent is a suspension of an alkylation catalyst and one or more hydrocarbons.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "boot" refers to a device for receiving a portion of a fluid having two or more phases. Typically, the fluid can be a suspension. Generally, the device allows separation of a heavier, denser phase from a lighter phase by using gravity. Particularly, the heavier, denser phase can be allowed to settle in the bottom of the boot and be removed using any suitable mechanism, such as gravity, a pump, or an ejector. The boot can include an enclosure, such as a pipe, optionally with an outlet for receiving a heavier, denser phase, and the boot may optionally include other equipment such as one or more valves and an orifice plate.

As used herein, the term "line" or "pipe" can be interchanged. Particularly, a line or pipe can generally refer to a cylindrical tube made from any suitable material, such as carbon steel, stainless steel, or a nickel alloy sold under trade designation MONEL by Inco Alloys International Inc. of Huntington, W. Va.

As used herein, the term "coupled" can mean two items, directly or indirectly, joined, fastened, associated, connected, or formed integrally together either by chemical or mechanical means, by processes including stamping, molding, or welding. What is more, two items can be coupled by the use of a third component such as a mechanical fastener, e.g. a screw, a nail, a bolt, a staple, or a rivet; an adhesive; or a solder.

As used herein, the term "substantially horizontal" means an orientation sufficiently proximate to horizontal so a denser fluid can separate from a heavier fluid and reside proximate to the bottom of a vessel, a line, a pipe, or other structure.

DETAILED DESCRIPTION

Generally, the embodiments disclosed herein pertain to an alkylation unit and a process. The alkylation process can be carried out either as a batch or continuous operation, although it is generally preferable to carry out the process continuously. In continuous operations, reactants along with the alkylation catalyst can be maintained at sufficient pressures and temperatures in a liquid phase and then continuously forced through dispersion devices into at least one alkylation reaction zone. The dispersion devices can be one or more jets, nozzles, porous thimbles or static mixers that can optionally create a turbulent flow. After a sufficient period of time, the alkylation product can be continuously separated from the catalyst and the alkylation catalyst may be separated and recycled to the at least one alkylation reaction zone. Optionally, at least a portion of the catalyst can be continuously regenerated and returned to the at least one alkylation reaction zone. Exemplary alkylation units and processes suitable for application of the mechanisms and devices discussed herein are disclosed in, e.g., U.S. Pat. Nos. 5,098,668 and 6,303,843 B1.

Figure 1:
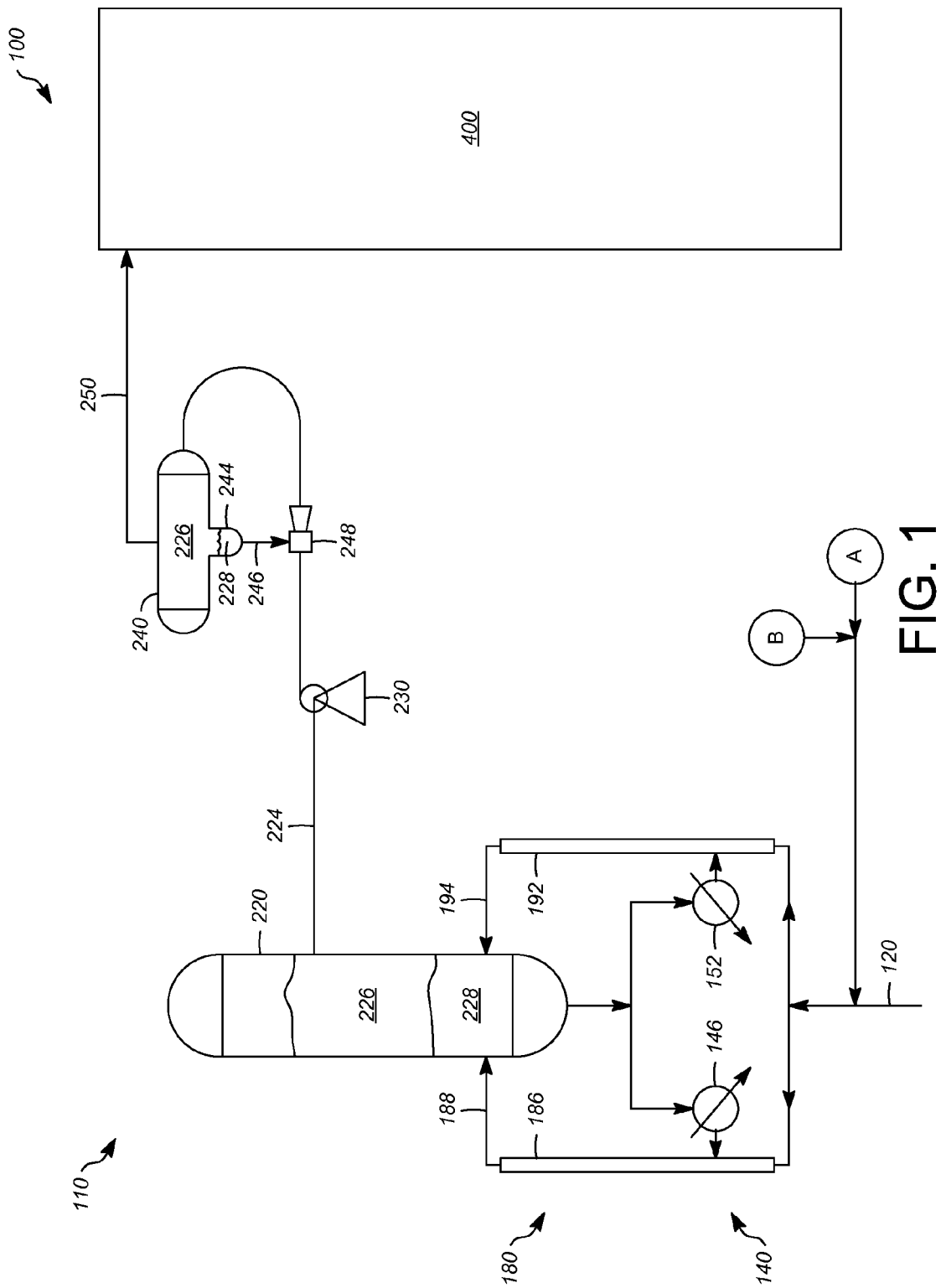
FIG. 1 is a schematic depiction of an exemplary unit with two of the vessels schematically depicted in cross-section to reveal a fluid having two phases.

Referring to FIG. 1, one exemplary alkylation unit 100 can include one or more vessels 110 and a fractionation zone 400. As depicted, process flow lines in the figures can be referred to as lines, pipes or streams. Particularly, a line or a pipe can contain one or more streams, and one or more streams can be contained by a line or a pipe.

The one or more vessels 110 can include at least one cooler 140, at least one alkylation reaction zone 180, a settler 220, and an acid recontactor 240. Generally, a feed 120 is provided that receives one or more recycle streams containing, respectively, isobutane and an alkylation catalyst at "A" and "B", as hereinafter described.

Generally, the feed 120 includes two phases, namely a hydrocarbon phase and an alkylation catalyst phase. The feed can include about 60 to about 10%, by volume, of the hydrocarbon phase and about 40 to about 90%, by volume, of the alkylation catalyst phase, based on the total volume of the feed. Typically, the hydrocarbon phase includes one or more hydrocarbons, such as a combination of one or more olefins and one or more isoparaffins. Usually, the isoparaffin to olefin molar ratio is about 2:1 to about 25:1, preferably about 5:1 to about 20:1. The hydrocarbon phase can include other compounds, such as normal paraffins, e.g., normal butane, propane, and ethane, in amounts of generally less than about 5%, by volume.

The alkylation catalyst can include a hydrogen fluoride, a hydrogen chloride, a hydrogen bromide, or a mixture thereof. The alkylation catalyst can be in anhydrous form or an acid solution that may include a small amount of water. Preferably, the alkylation catalyst is hydrogen fluoride. Typically, the amount of water present in the hydrogen fluoride and water solution is no more than about 30%, preferably less than about 10%, and more preferably less than about 5% based on the total weight of the solution. As described hereinafter, the alkylation catalyst is hydrofluoric acid, although it should be understood that any suitable alkylation catalyst may be utilized.

The at least one alkylation reaction zone 180 can include a first reactor 186 and a second reactor 192. Although the alkylation reactors 186 and 192 are depicted as vessels having a greater diameter than the associated piping, it should be understood that the alkylation reactors 186 and 192 can be fashioned to be the same diameter as the associated piping or any other suitable diameter. Generally, the alkylation reaction temperature can range from about −20 to about 70° C., preferably about −5° to about 55° C. Typically, the reaction occurs in a liquid phase at a pressure of about 380 to about 1,200 kPa. The olefin space velocity can range from about 0.1 to about 200 volumes olefin per volume per hour of the hydrofluoric acid (v/v/hr), with a contact time of the one or more hydrocarbons and hydrofluoric acid can be about 0.05 to about 60 minutes. Effluents 188 and 194 from the respective first reactor 186 and the second reactor 192 can include one or more hydrocarbons and the hydrofluoric acid. The one or more hydrocarbons can include propane, normal butane, isobutane, and an alkylate product of $C_7$ and/or $C_8$ isoalkanes, such as trimethylpentanes and dimethylhexanes. The volumetric ratio of hydrofluoric acid to alkylation product generally does not exceed about 2:1, and can range from about 0.25:1 to about 2:1. The one or more hydrocarbons can form a suspension and be sent to the settler 220.

The settler 220 can operate at a temperature of about −20° to about 125° C., preferably about 0° to about 80° C. and a pressure of about 50 to about 3,100 kPa, preferably about 95 to about 2,600 kPa. Generally, the one or more hydrocarbons and the hydrofluoric acid in the settler 220 form two phases via gravity, namely a lighter hydrocarbon phase 226 and a heavier acid phase 228. The heavier acid phase 228 can settle in the bottom of the settler 220 and may be continually removed from the lower portion of the settler 220 and passed to the at least one cooler 140 for recycling to the at least one reaction zone 180. The at least one cooler 140 can include a first cooler 146 and a second cooler 152. Generally, the first and second coolers 146 and 152 are heat exchangers utilizing cooling water to reduce the temperature of the acid catalyst. Thus, the first and second coolers 146 and 152 can receive the hydrofluoric acid from the settler 220 and recycle the cooled acid to, respectively, the alkylation reactors 186 and 192 for catalyzing reactions. Hence, the first and second coolers 146 and 152 can aid in controlling the reaction rate in the alkylation reaction zone 180.

The lighter hydrocarbon phase 226 can be withdrawn as an effluent through a line 224 and sent via a pump 230 to the recontactor 240. Generally, the recontactor 240 can reduce the amount of halide, in this instance fluoride, ions present in this effluent by recombining the ions into, e.g., hydrogen fluoride. In some exemplary alkylation units, the recontactor 240 may be omitted and the effluent can be sent directly to the fractionation zone 400.

Typically, this effluent in the line 224 can still have some acid present. The effluent can pass from an outlet of the pump 230 to an ejector, such as an eductor 248, and can serve as the motive fluid. The hydrofluoric acid 228 from a boot 244 of the recontactor 240 can be provided to an inlet of the eductor 248, as hereinafter described. The hydrofluoric acid 228 can be mixed with the hydrocarbon phase 226 and exit the eductor 248, and then enter the recontactor 240.

In the recontactor 240, the hydrofluoric acid in the hydrocarbon phase can separate via gravity and settle in the recontactor boot 244 that is drained to the eductor 248. The recontactor 240 can operate at a temperature of about −20° to about 125° C., preferably about 0° to about 80° C. and a pressure of about 50 to about 3,100 kPa, preferably about 95 to about 2,600 kPa. Although acid in suspension in the hydrocarbon phase 226 can supply the acid to the boot 244, additional acid can be added to the recontactor 240 or a line 246 communicating with the eductor 248. An effluent including one or more hydrocarbons 226 can exit the recontactor 240 through a line 250 to the fractionation zone 400.

Figure 2:
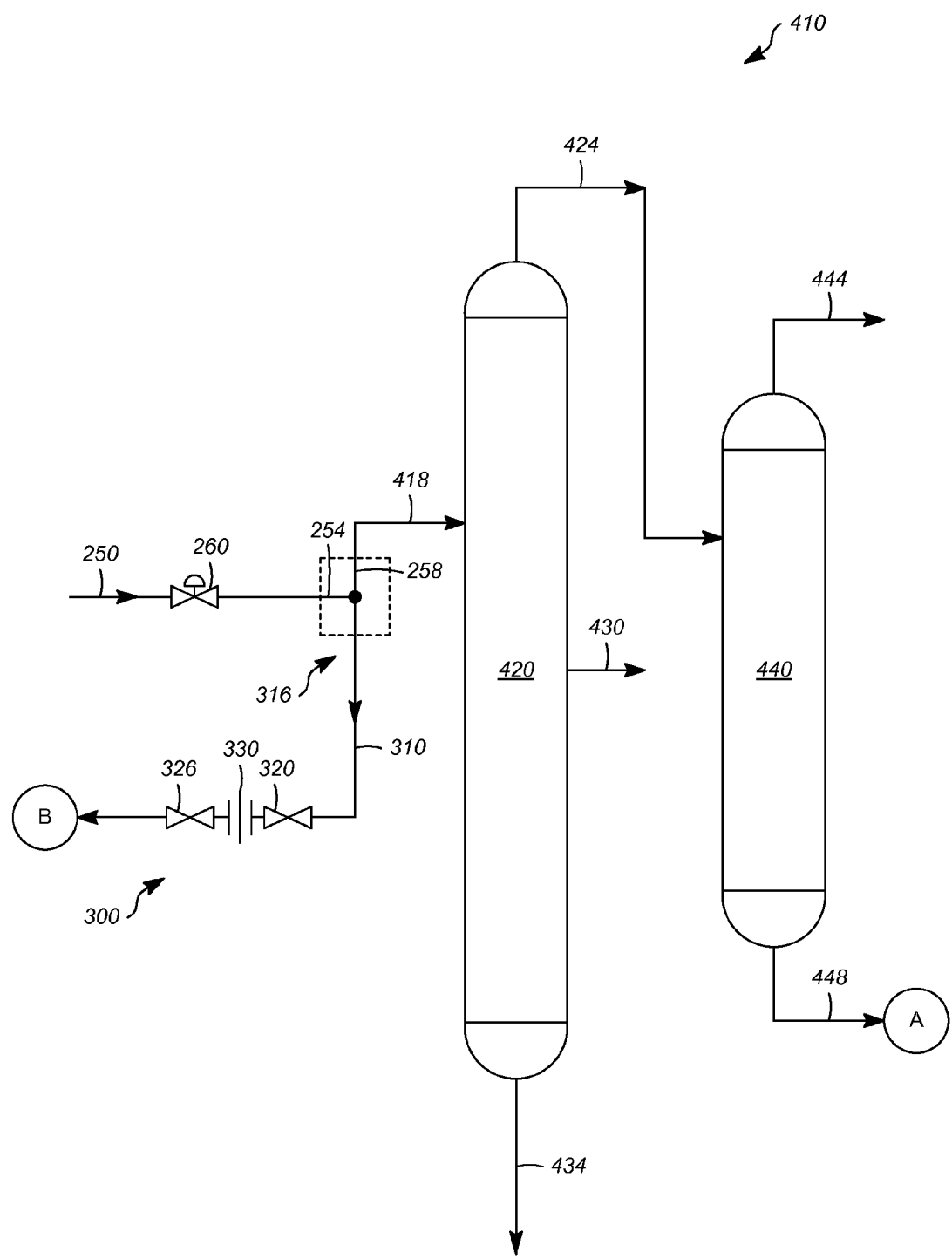
FIG. 2 is a schematic depiction of one or more distillation columns.
Figure 6:
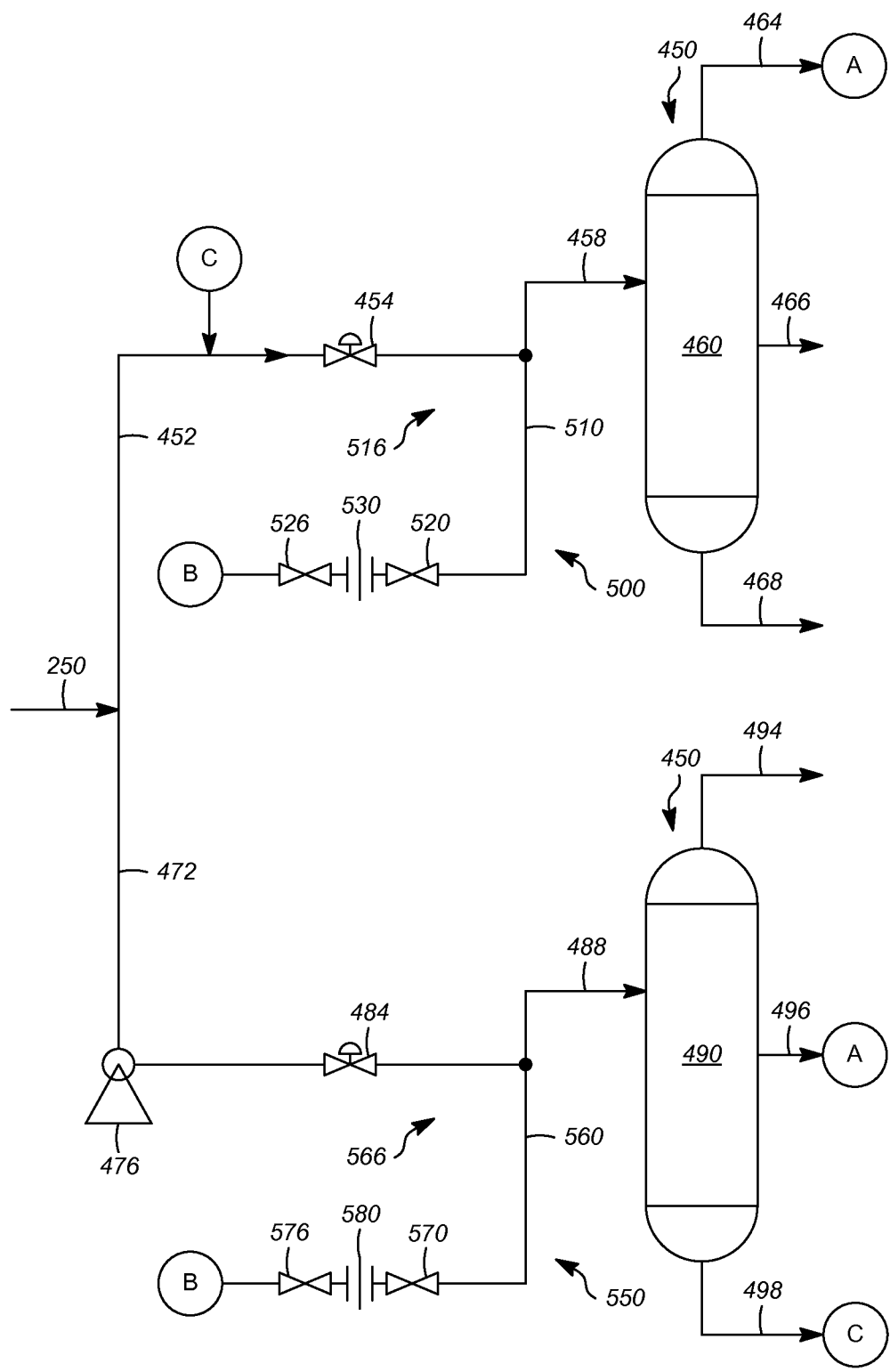
FIG. 6 is a schematic depiction of a plurality of distillation columns.

The fractionation zone 400 can include any suitable equipment for separating the effluent in the line 250 into various fractions. Preferably, the fractionation zone 400 can utilize overhead condensers, pumps, furnaces, reboilers, and at least one, preferably a plurality of distillation columns. Moreover, the distillation columns in the fractionation zone 400 can operate at any suitable temperature and pressure to separate the one or more hydrocarbons into various hydrocarbon products. Referring to FIGS. 2 and 6, two alternative, preferred embodiments of vessels and equipment for a fractionation zone 400 are depicted.

Referring to FIG. 2, in this exemplary embodiment, the fractionation zone 400 can include a boot 300 and one or more distillation columns 410. In this exemplary embodiment, the boot 300 can include a pipe 310, a first valve 320, a second valve 326, and an orifice plate 330. Alternatively in other embodiments, the boot 300 can consist of an enclosure, such as a pipe, optionally with an outlet. Typically, the pipe 310 is coupled to the line 250 having a substantially horizontal portion 254 and a, preferably substantially vertical, run 258. Generally, the line 250 provides the effluent from the recontactor 240 through a first valve 260, which in turn communicates with a line 418. The pipe 310 of the boot 300 is coupled to the line 250, preferably at the horizontal portion 254 proximate to the run 258, at any suitable angle, such as an angle of about 45° to about 135°, preferably about 90°. Typically, the angle 316 is perpendicular.

Figure 3:
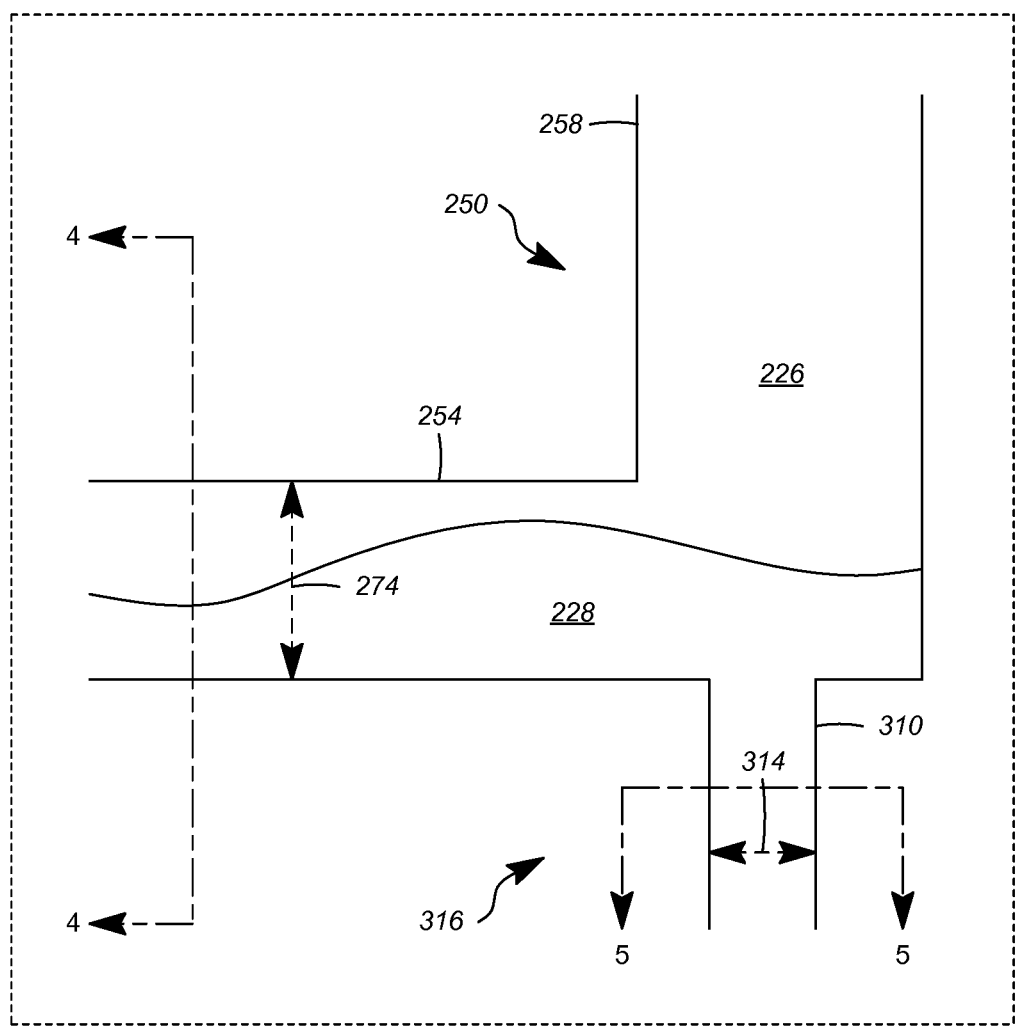
FIG. 3 is a schematic depiction of the highlighted area in FIG. 2.
Figure 4:
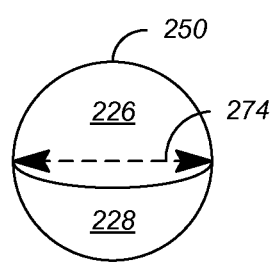
FIG. 4 is a cross-sectional depiction along a line 4-4 of FIG. 3.
Figure 5:
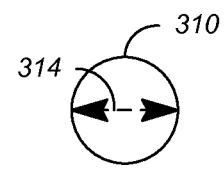
FIG. 5 is a cross-sectional depiction along a line 5-5 of FIG. 3.

Referring to FIGS. 3-5, a schematic depiction is provided of the coupling of the line 250 with the pipe 310. The amount of acid is exaggerated for illustrative purposes only. Generally, the effluent in the line 250 can include up to about 5%, by volume, typically about 2 to about 3%, by volume of a hydrofluoric acid. Particularly, if the settler 220 and/or the recontactor 240 are undersized, or excessive feed 120 and corresponding amounts of hydrofluoric acid are provided to the alkylation unit 100, hydrofluoric acid can carry over to the fractionation zone 400 and corrode vessels and other equipment. Thus, the boot 300 can receive the hydrofluoric acid that settles in the pipe 310. Although hydrofluoric acid can be present in any amount and other compounds can be present, typically the fluid in the pipe 310 is rich in or substantially hydrofluoric acid.

Usually, the run 258 can be any suitable angle with respect to the substantially horizontal portion 254 to separate the effluent in the line 250. Specifically, the effluent may divide into a first portion of one or more hydrocarbons 226 and a second portion of the hydrofluoric acid 228 that can settle at the bottom of the line 250. Preferably, the run 258 extends to a higher elevation and can be substantially vertical to form an elbow with the substantially horizontal portion 254 to act as a settler to separate the one or more hydrocarbons and hydrofluoric acid. Generally, the horizontal or level portion 254 is proximate to the pipe 310. Desirably, the horizontal portion 254 is of sufficient length to allow the settling of the hydrofluoric acid with respect to the one or more hydrocarbons to allow the separation of the hydrofluoric acid by gravity. Usually, the horizontal portion 254 can be about 50 meters, about 20 meters, about 10 meters, or less. As a result, the hydrofluoric acid 228 can flow freely into the boot 300.

In addition, the line 250 and the pipe 310 can be of any suitable dimension. Referring to FIGS. 4 and 5, the line 250 and the pipe 310 can have respective diameters 274 and 314, and preferably each of the line 250 and the pipe 310 has a uniform diameter. Particularly, the line 250 and the pipe 310 can have any suitable size, and typically each diameter 274 and 314 is, independently, less than about 1.0 meter, less than about 0.75 meter, less than about 0.5 meter, or less than about 0.25 meter in diameter. Generally, the ratio of the diameter 274 of the line 250 to the diameter 314 of the pipe 310 is from about 8:1 to about 1:8, preferably about 8:1 to about 4:1.

Referring to FIG. 2, the hydrofluoric acid can flow into the pipe 310 and be routed through the valves 320 and 326 to the orifice plate 330. The valves 320 and 326 can isolate the orifice plate 330 for replacing the plate 330 after, e.g., the expiration of its service life. The orifice plate 330 can be sized based on the calculated amounts of hydrofluoric acid in the effluent of the line 250. Alternatively, another flow regulating device, such as a control valve, may be used instead of the orifice plate 330. Particularly, the hydrofluoric acid 228 can be recycled at "B" to be combined with the feed 120 before entering the at least one alkylation reaction zone 180. If desired, any suitable fluid transfer device, such as a pump or an ejector, can be used to recycle the hydrofluoric acid.

Afterwards, the one or more hydrocarbons 226 from the run 258 and the line 418 can enter the one or more distillation columns 410. The one or more distillation columns 410 can include a primary column 420 and a secondary column 440 orientated in series. The primary column 420 can include an overhead stream 424, a side stream 430, and a bottom stream 434. Generally, the side stream 430 is rich in or substantially a normal butane product and the bottom stream 434 is rich in or substantially an alkylate product, such as $C_7$ and/or $C_8$ isoalkanes. Typically, these products can be moved to other units within a refinery or petrochemical manufacturing facility to be used in other processes or sent to be blended with other products. The overhead stream 424 can be rich in or substantially isobutane and propane. As such, the overhead stream 424 can be routed to the secondary column 440. An overhead stream 444 of the secondary column 440 can be rich in or substantially propane and the bottom stream 448 of the secondary column 440 can be rich in or substantially isobutane. The bottom stream 448 can be recycled to the feed 120 at "A" of the one or more vessels 110. The overhead stream 444 can be again utilized as a product or be sent for further processing.

Referring to FIG. 6, another exemplary embodiment of vessels and equipment for the fractionation zone 400 is depicted. Generally, this embodiment can include a plurality of columns 450, which can include a first column 460 and a second column 490 orientated in parallel, a first boot 500, and a second boot 550. The boot 500 can include a pipe 510, orientated at any suitable angle 516, a first valve 520, a second valve 526, and an orifice plate 530. In addition, the boot 550 can include a pipe 560, orientated at any suitable angle 566, a first valve 570, a second valve 576, and an orifice plate 580. Both the boots 500 and 550 can be substantially similar to the boot 300 described above. The line 250 can provide a feed that is split with one portion traveling through a line 452 and a second portion traveling through a line 472. Generally, these portions can be substantially equal.

Referring to line 452, the one or more hydrocarbons can travel through a valve 454 and pass the boot 500. As described above, the hydrofluoric acid can be separated from the one or more hydrocarbons by the boot 500, and recycled at "B" to the feed 120. The alkylation catalyst, such as hydrofluoric acid or hydrogen fluoride, can be present in the boot 500 in any concentration, such as greater than about 50%, about 60%, or about 70%, by weight, or less than about 20%, about 10%, about 5%, or even about 2%, by weight, based on the total weight of the fluid in the boot 500. The one or more hydrocarbons can travel through a line 458 to a first column 460 of the plurality of columns 450.

The first column 460 can receive one or more hydrocarbons in a line 458 and is generally an isostripper. The first column 460 can provide an overhead stream 464 rich in or substantially isobutane, a side stream 466 rich in or substantially normal butane, and a bottom stream 468 rich in or substantially a $C_7$ and/or $C_8$ isoalkane product. The side stream 466 and the bottom stream 468 can be routed to other units for further processing or utilized in various products. The overhead stream 464 that is rich in or substantially isobutane can be recycled to the feed 120 at "A".

Referring to the portion traveling through the line 472, the one or more hydrocarbons can travel through the pump 476 and through a valve 484, and pass the boot 550. As described above, the hydrofluoric acid can be separated from the one or more hydrocarbons by the boot 550, and recycled at "B" to the feed 120. The alkylation catalyst, such as hydrofluoric acid or hydrogen fluoride, can be present in the boot 550 in any concentration, such as greater than about 50%, about 60%, or about 70%, by weight, or less than about 20%, about 10%, about 5%, or even about 2%, by weight, based on the total weight of the fluid in the boot 550. Subsequently, the one or more hydrocarbons can travel through a line 488 to the second column 490. The second column 490 can be a depropanizer Generally, the second column 490 can provide an overhead stream 494 that is rich in or substantially propane, a side stream 496 that is rich in or substantially isobutane, and a bottom stream 498 that is rich in or substantially a $C_7$ and/or $C_8$ isoalkane product. Generally, the overhead stream 494 can be routed to other units for further processing or be used as a product. The side stream 496 that is rich in or substantially isobutane can be recycled at "A" to the feed 120 similarly as the stream 464 as described above.

The bottom stream 498 that is rich in or substantially $C_7$ and/or $C_8$ isoalkane product can be recycled at "C" to the line 452 to be combined with the one or more hydrocarbons in the line 452 and sent to the first column 460, as described above.

The one or more boots coupled to a respective line as described herein can remove alkylation catalyst from one or more hydrocarbons to prevent corrosion of downstream equipment. Although such boots have been described as being in a fractionation zone, the one or more boots can be positioned in any suitable location to remove the alkylation catalyst from the one or more hydrocarbons provided to a fractionation zone, or other downstream zone or equipment.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for separating an alkylation catalyst from one or more hydrocarbons comprising:
    a) providing the one or more hydrocarbons and the alkylation catalyst to a an alkylation reaction zone;
    b) providing an effluent from the alkylation reaction zone to a settler; and
    c) receiving an effluent from the settler to a fractionation zone through a line wherein the line is coupled to a pipe to remove a stream comprising at least a portion of a settled alkylation catalyst, and the line is orientated substantially horizontal proximate to the pipe, wherein the stream is rich in or substantially alkylation catalyst.

2. The process according to claim 1, wherein the alkylation catalyst comprises hydrogen fluoride or an acid solution thereof.

3. The process according to claim 1, wherein the alkylation catalyst is at least partially recycled to at least one alkylation reaction zone.

4. The process according to claim 1, wherein the fractionation zone comprises one or more distillation columns.

5. The process according to claim 1, wherein the fractionation zone comprises a plurality of distillation columns.

6. The process according to claim 1, wherein a ratio of a diameter of the line to a diameter of the pipe is from about 8:1 to about 4:1.

* * * * *